United States Patent [19]

Aoki et al.

[11] Patent Number: 5,503,416
[45] Date of Patent: Apr. 2, 1996

[54] UNDERCARRIAGE FOR X-RAY DIAGNOSTIC EQUIPMENT

[75] Inventors: Gary Aoki, Murray; Timothy D. Bowman, Salt Lake City, both of Utah

[73] Assignee: OEC Medical Systems, Inc., Salt Lake City, Utah

[21] Appl. No.: 208,984

[22] Filed: Mar. 10, 1994

[51] Int. Cl.⁶ .............................. B62B 3/00; B60B 33/00
[52] U.S. Cl. .................... 280/79.11; 280/47.34; 280/62; 378/193; 378/198; 16/35 R
[58] Field of Search ............... 280/47.11, 47.34, 280/62, 250.1; 378/193, 195, 196, 197, 198; 16/22, 23, 35 R, 31 R; 188/112

[56] References Cited

U.S. PATENT DOCUMENTS

| | | | |
|---|---|---|---|
| 3,790,805 | 2/1974 | Foderaro | 378/198 |
| 3,988,800 | 11/1976 | Sachser | 16/35 R |
| 4,722,114 | 2/1988 | Neumann | 16/35 R |
| 4,802,197 | 1/1989 | Juergens | 378/198 |
| 4,955,046 | 9/1990 | Siczek et al. | |
| 4,979,202 | 12/1990 | Siczek et al. | |
| 5,008,921 | 4/1991 | Kaul et al. | 378/193 |
| 5,050,204 | 9/1991 | Siczek et al. | |
| 5,067,145 | 11/1991 | Siczek et al. | |
| 5,081,662 | 1/1992 | Warden et al. | 378/196 |
| 5,176,393 | 1/1993 | Robertson et al. | 280/250.1 |
| 5,303,450 | 4/1994 | Lange | 16/35 R |
| 5,351,774 | 10/1994 | Okamoto | 180/907 |

FOREIGN PATENT DOCUMENTS 0235834  9/1987  European Pat. Off. ............... 378/198

OTHER PUBLICATIONS

ACE Controls, Inc.© 1992 Catalogue.

*Primary Examiner*—Margaret A. Focarino
*Assistant Examiner*—Min S. Yu
*Attorney, Agent, or Firm*—Thorpe, North & Western

[57] ABSTRACT

An undercarriage for heavy diagnostic equipment having a selectably engageable swivel mechanism activated by the movement of a cam to allow the undercarriage to be turned when desired and rolled in a straight line when necessary, a selectably engageable braking mechanism to prevent movement of the undercarriage when desired, but allowing the undercarriage to be moved quickly if needed, and a balance wheel assembly to prevent the undercarriage and equipment from becoming unstable when encountering obstacles, while allowing the undercarriage to be rolled up inclines. An aspect of the invention allows the swivel and braking mechanisms to be selectively engaged from the same point along the undercarriage, thereby providing superior control of the undercarriage and the equipment which it carries.

30 Claims, 11 Drawing Sheets

UNDERCARRIAGE FOR X-RAY DIAGNOSTIC EQUIPMENT

BACKGROUND OF THE INVENTION

The present invention relates to an improved undercarriage for mobile X-ray diagnostic equipment, and in particular to a combination of balance, brake and swivelling devices of the undercarriage which provide enhanced control over the equipment during movement thereof.

Large medical diagnostic equipment such as X-ray machines serve an important part in the medical community's ability to diagnose and treat disease. The expense of these machines, however, places limitations on the number that a hospital or other medical facility can afford to purchase. Thus, hospitals often use mobile equipment which can be moved from one place to another as needed, alleviating the need for having a machine at every diagnostic location.

The movement of this equipment, however, raises numerous problems due to the equipment's size and weight. A C-arm X-ray machine, for example, can weigh in excess of six hundred pounds. Additionally, the C-arm portion of such equipment is usually about six feet tall, six feet long, and three feet wide. Because of the size and weight of the equipment, the only practical means for moving it is to provide wheels on the base of the machine.

These wheels are often designed to swivel to facilitate turning the equipment within a room or hallway, but such swiveling wheels can themselves cause problems. For example, if the equipment is moved too quickly, or on surface that is sloped, the wheels may turn slightly, causing the equipment to drift to one side or even turn sideways. This, in turn, may result in the equipment tipping over and being damaged.

Additionally, the method for moving the X-ray C-arm must be adjustable to provide precise movement when in use. Some surgical procedures require that numerous X-rays be taken in the same place, and some require X-rays to be taken at various points along the patient's body. The C-arm's base must include mechanisms to allow the C-arm to be held in a fixed position when desired, and to move in a relatively straight line (forward and back or to either side) when necessary. Additionally, the equipment must be easily movable without interfering with the medical personnel in the operating room.

An improved undercarriage supporting the C-arm would allow the wheels to swivel when desired, while allowing the user to lock the wheels in one or more directional orientations either to avoid lateral drift when transporting the equipment or force the equipment along a linear path perpendicular to the length of the machine during a surgical procedure. An improved undercarriage would also allow the wheels to be locked to keep the equipment in place while allowing simple and quick release of the lock so that the equipment may be moved out of the way.

Bumps and uneven surfaces in hospital hallways cause other problems in moving large diagnostic equipment. A small bump such as the base of a door frame can create a significant problem for those moving X-ray C-arms and other large machines. Due to the equipment's weight, it is difficult to lift the front wheels of the undercarriage over even these small bumps. To solve the problem, the rear wheels of the undercarriage are commonly placed as close as possible to the center of gravity of the equipment to facilitate lifting of the front wheels when needed. This positioning, however, renders the equipment less stable. With such an arrangement, an unexpected bump can cause the front wheels to rise, shifting the equipment's center of gravity and causing the equipment to rock backwards, jarring the equipment and potentially injuring the feet or legs of those moving the machine.

In an attempt to solve this problem, prior innovators have placed stoppers near the back of the undercarriage to prevent the equipment from rocking backwards. The stoppers, however, interfere with certain movements of the machine, such as when it is necessary to roll the machine up an incline. As the front wheels rise up the incline, the machine pivots backward, the stoppers grip the floor, and the machine is prevented from forward movement. An improved undercarriage is needed which allows the equipment to pass over obstacles and roll up inclines, while preventing the equipment from suddenly rocking backwards.

OBJECTS AND SUMMARY OF THE INVENTION

It is therefore an object of this invention to provide an undercarriage for X-ray or other diagnostic equipment having improved control during moving.

It is an additional object of the invention to provide an undercarriage in which some of the wheels selectively can swivel to allow turning of the equipment, or lock so as to limit the equipment to movement along a linear path.

It is another object of the invention to provide a wheel brake which prevents the wheel from rotating when the brake is in an engaged position.

It is a further object of the invention to combine a wheel brake and swivel lock mechanism for efficiency and ease of use.

It is an additional object of the invention to provide a undercarriage for X-ray diagnostic equipment in which the swivel lock can be engaged in unison with the wheel brake or independently.

It is yet another object of the invention to provide an undercarriage for large diagnostic equipment which prevents the equipment from becoming unstable when traveling over irregular or inclined surfaces.

It is another object of the invention to provide an undercarriage which protects the feet and legs of those moving large diagnostic equipment from being injured by sudden shifts in the equipment's center of gravity.

It is an additional object of the invention to provide an undercarriage which enables the diagnostic equipment to be transported up inclines without interference from the undercarriage assembly.

These and other objects of the invention are disclosed in a preferred embodiment of an improved undercarriage for X-ray diagnostic equipment. The undercarriage has a conventional base member for supporting the diagnostic equipment, including a wheeled support arm extending forwardly from the base member to provide support and stability for the equipment. At least one wheel is attached to the base member by a selectively engageable swivel mechanism which allows the wheel to swivel or to be locked in at least one direction, and a braking mechanism which prevents the wheel from rolling when movement is not desired. The brake and swivel lock are both engaged by the same mechanism, allowing both to be engaged at once, if desired.

A preferred embodiment of the undercarriage also includes a balance wheel assembly positioned behind the rear wheels to prevent the equipment from rocking backwards when encountering bumps. The balance wheel assembly includes a small retractable leg attached to a wheel and a controlled velocity damping device connected to the leg to provide a resistance force which prevents sudden movements of the leg while allowing the leg to slowly retract into the base member, enabling the equipment to be rolled up inclines.

BRIEF DESCRIPTION OF THE DRAWINGS

The above objects, aspect, and embodiments of the present invention will be described with reference to the accompanying drawing figures, of which.

DETAILED DESCRIPTION OF THE INVENTION

A preferred embodiment of the present invention is described in relation to an undercarriage designed to support and transport a mobile C-arm X-ray diagnostic machine. The invention can also easily be used with other types of medical equipment and similar devices.

Figure 1:
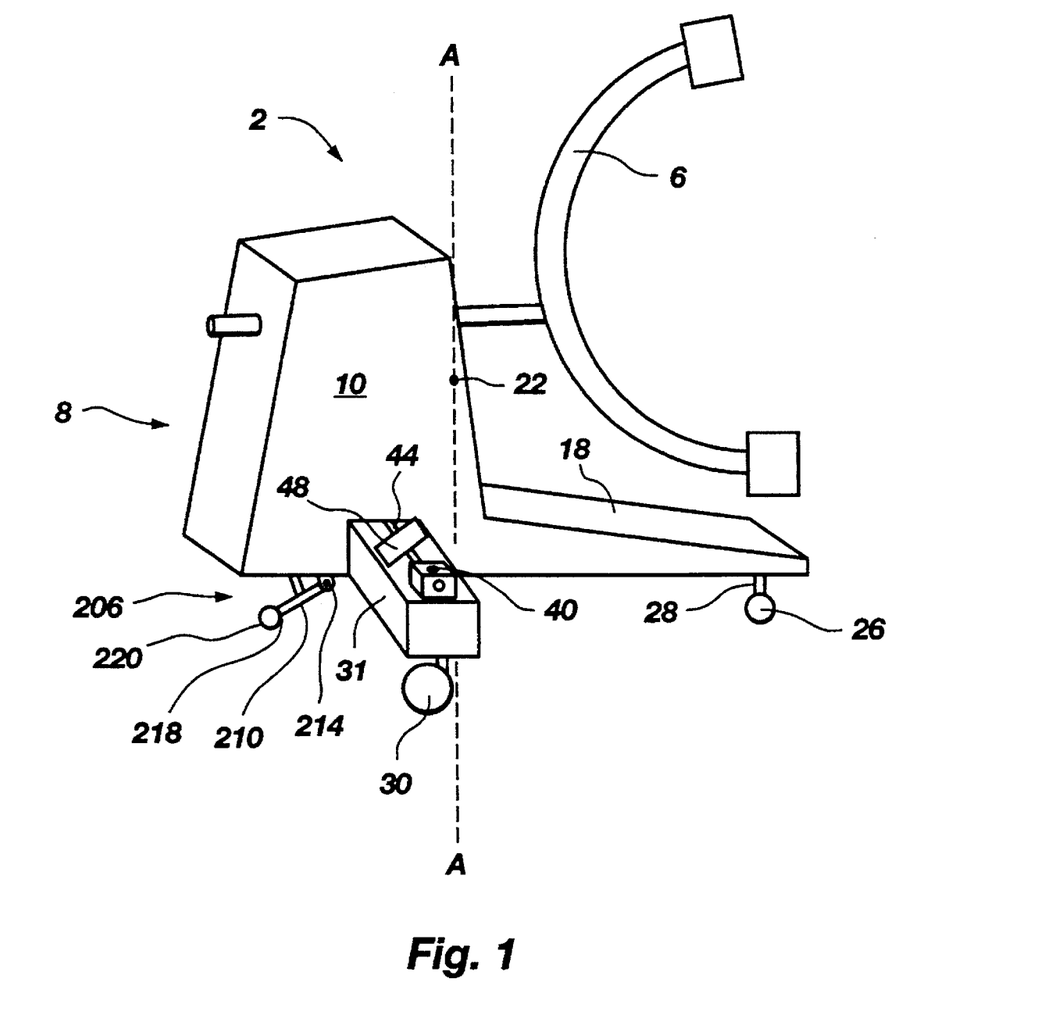
FIG. 1 is a side elevational view of the undercarriage of the instant invention as used with C-arm X-ray diagnostic equipment.

Referring to FIG. 1, a mobile C-arm X-ray machine 2 includes a C-arm 6, whose structure is known to those skilled in the art, and an undercarriage 8. The C-arm 6 is of conventional make and can be substituted with other types of diagnostic or general medical equipment while retaining the advantages of the invention.

The undercarriage 8 includes a base 10 which supports the C-arm. A support arm 18 extends forwardly from the base 10, attaching to the latter at a point slightly forward of a vertical plane A—A passing through the center of gravity of the machine 2. The support arm 18 is positioned so as to be under the C-arm 6 to prevent the x-ray machine 2 from falling forward.

A front wheel 26 is attached by a rod 28 to the bottom of the front end of the support arm 18. The exact size of the front wheel 26 will depend on conventional design considerations such as the size and weight of the equipment which the undercarriage 8 supports.

The rod 28 can be adapted to rotate about a vertical axis so that the front wheel 26 swivels, or the rod can alternatively be fixed in place to prevent swiveling of the wheel. A swiveling attachment allows for easy turning of the equipment in narrow spaces and, in conjunction with swiveling rear wheels, enables the undercarriage to move laterally. A fixed attachment provides improved directional control when moving the equipment in a straight line, particularly when the equipment is heavy or is moved rapidly. As will be explained below, the front wheel 26 swivels in the preferred embodiment. Types of swiveling attachments other than the rod 28 will be known to those skilled in the art.

At least one rear wheel 30 is mounted to the bottom of the base 10 to enable the C-arm or other machine to be wheeled across a surface in tandem with the front wheel 26. The undercarriage has two wheels 30 in the preferred embodiment, the wheels being affixed to either end of a cross member 31 which extends laterally through the bottom of the base 10. The placement of the rear wheels 30 provides lateral stability to the undercarriage 8 and the equipment it carries, decreasing the likelihood of the machine 2 tipping over when bumped or moved around a corner.

In the preferred embodiment, the rear wheels 30 are disposed just rearward of the vertical plane A—A going through the machine's center of gravity to facilitate lifting of the support arm 18 when the front wheel 26 encounters a bump or other obstacle. If the rear wheels 30 are placed substantially rearward of the plane A—A, the support arm 18 is difficult to lift due to the weight of the machine 2.

In the preferred embodiment, the rear wheels 30 can selectively be adapted to swivel, limit themselves to forward/rearward movement, or limit themselves to lateral movement. An embodiment of a locking mechanism according to the invention which can selectively be engaged to carry out those functions will be described below. The rear wheels 30 preferably also have a brake positioned adjacent each wheel selectively to lock the wheels against rolling movement. One embodiment of such a brake is described below.

A cam shaft 44 extends along the cross member 31 and rotates cam 40 disposed above each of the wheels 30. A pedal 48 is attached to the cam shaft 44 and extends tangentially from the cam shaft in such a way as to allow the cam shaft to be rotated in either direction by placing downward pressure on an end of the pedal. The effects of rotating the cam 40 are explained in more detail below.

The pedal 48 is positioned to facilitate the engagement and disengagement of the swivel lock and brake from either side of the machine 2, making it easier to use in the tight confines often encountered in hospitals and other medical facilities.

A balance wheel assembly 206 is positioned behind the rear wheels 30 and includes an elongate leg 210 which is pivotally attached at its proximal end 214 to the bottom of the base member 10 behind the cross member 31, and which is rotatably mounted to a wheel 220 on its distal end 218 so as to be rotatable about a horizontal axis. The balance wheel assembly 206 prevents the machine 2 from rocking backwards, in the event that the front wheel 26 contacts an obstacle. This is accomplished by means of a controlled velocity damper and other structural elements described in detail below.

Figure 2:
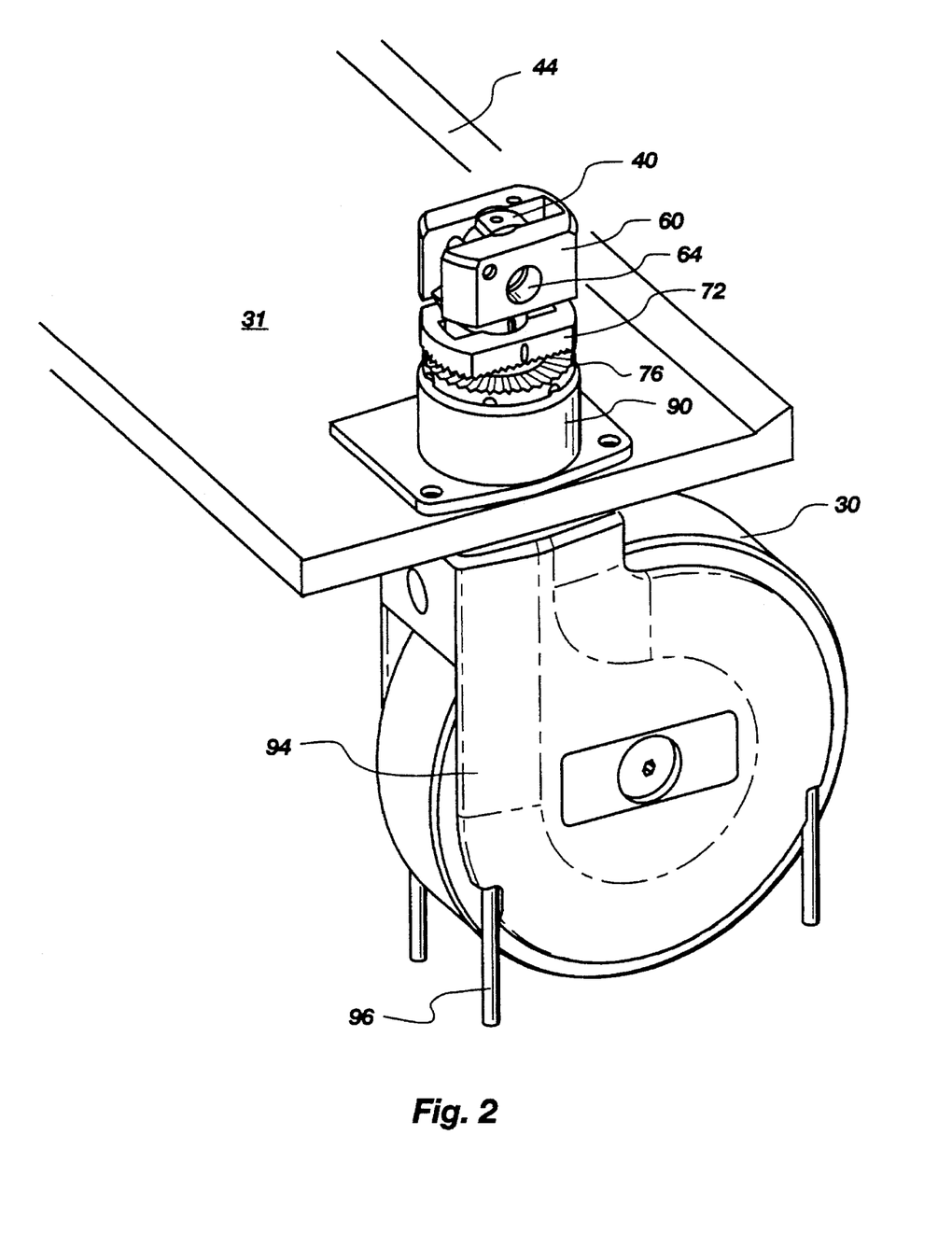
FIG. 2 is a perspective view of the wheel, brake, swivel and lock assemblies of the undercarriage of the instant invention.
Figure 3:
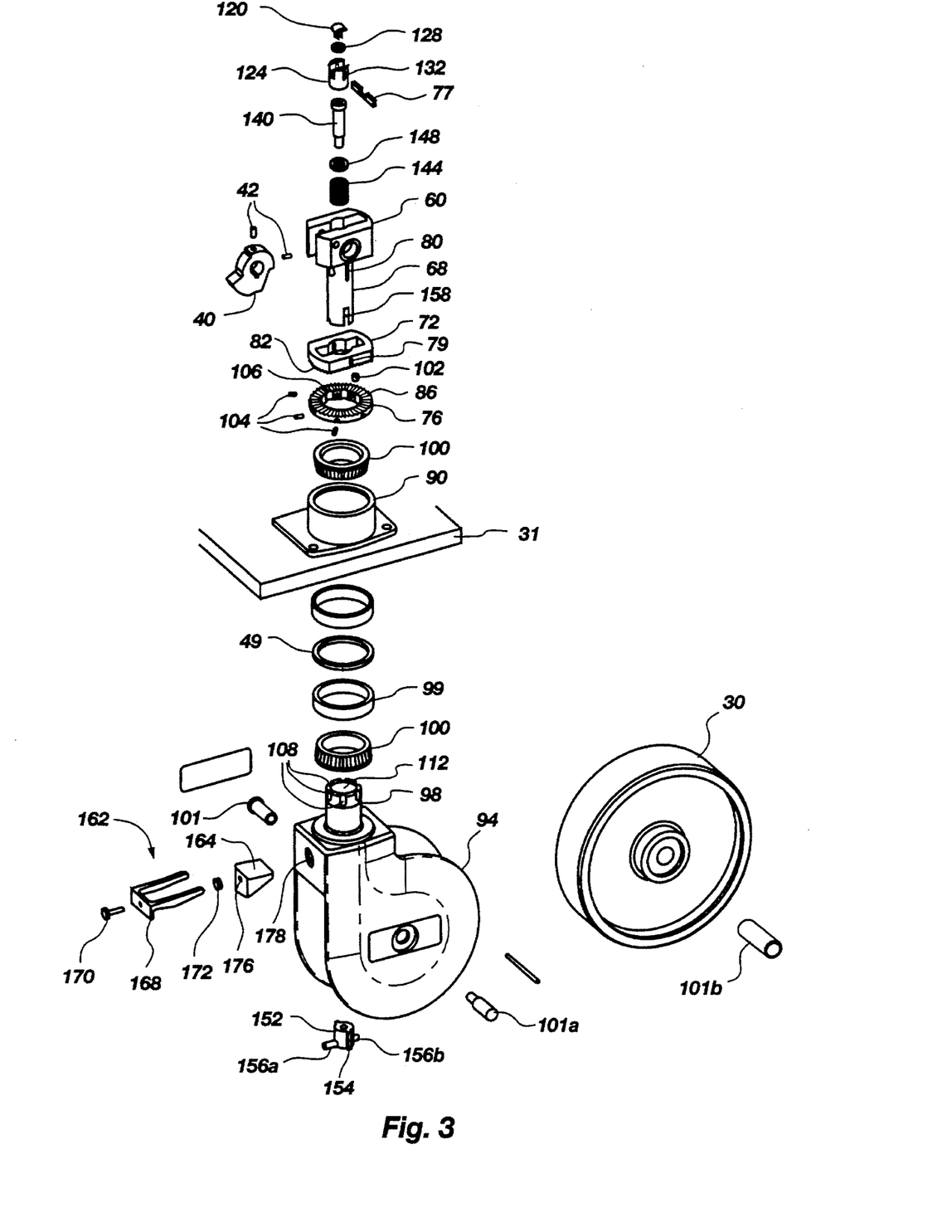
FIG. 3 is an exploded view of the wheel, brake, swivel and lock assemblies of FIG. 2.

Referring now to FIGS. 2 and 3, there is shown a perspective view (FIG. 2) and an exploded view (FIG. 3) of one of the rear wheels 30 and preferred embodiments of related brake, swivel and lock mechanisms according to the instant invention.

The cam 40 identified in FIG. 1 is positioned within a housing 60. A side of the housing 60 has a hole 64 to enable the cam shaft 44 (shown in FIG. 2 only) to slide through the cam 40. Two screws 42 secure the cam shaft 44 to the cam 40 so that rotation of the cam shaft 44 causes the cam 40 to rotate within the housing 60 to thereby engage or disengage the swivel and locking mechanisms.

A cylinder 68 attaches to the bottom of and extends downwardly from the housing 60. Rotation of the cam 40 causes movement in a plurality of structures located adjacent the cylinder 68, engaging or disengaging the swivel and braking mechanisms.

Positioned around the cylinder 68 below the housing 60 is a locking member 72 and a ring 76 disposed below the locking member. The locking member 72 has a plurality of teeth 82 on its lower side which interact with the upper surface of the ring 76 to prevent the ring from rotating, when desired. In a preferred embodiment, the upper surface of the ring 76 has a plurality of teeth 86 which form a complementary engagement with the teeth 82 of the locking member 72. Ideally, the teeth 82 and 86 are differentiated by less than six degrees so as to minimize relative movement of the locking member 72 and ring 76 when the teeth 82 and 86 are engaged. Alternatively, the upper surface of the ring may be provided with a pliable material, e.g., rubber or other elastomeric material, such that pressure between the teeth 82 of the locking member 72 and the upper surface of the ring 76 will prevent the ring from turning. Other arrangements are possible.

Rotation of the cam 40 into a specified position causes the structures within the cylinder 68 of the housing 60 to move downward. A small key 77 extends through a channel 80 in the cylinder 68 and into a recess 79 in the locking member 72. The downward movement of the structures within the cylinder 68 with the rotation of the cam causes the key to move downward, correspondingly causing the locking member 72 to contact the flange 76.

Located beneath the locking member 72 and the ring 76 is an outer sleeve 90. A flange 92 on the outer sleeve 90 attaches to the cross member 31. An inner sleeve 98 extends upwardly from the yoke 94 of the wheel and extends into the outer sleeve 90. Rings 99 and bearings 100, together with an appropriate lubricant, rotate between the inner sleeve 98 and the outer sleeve 90 to allow the rear wheel 30 to swivel. A small axle 101 connects the two sides of the yoke, and allows the rear wheel 30 to rotate.

As shown in FIG. 2, the yoke 94 can have a plurality of cable pushers 96 which prevent the wheel from catching on cables. If a cable falls from the equipment being carried, the wheel 30 may catch on the cable and either destroy the cable, or cause the undercarriage to come to a complete stop. The cable pushers 96 minimize the risk of either situation happening by preventing contact between the cable and the wheel.

Those skilled in the art will recognize in light of this disclosure that the mechanical structures described herein could be varied or modified to reach the same functions as those of the described embodiment.

The ring 76 is affixed to the inner sleeve 98 by a set screw 102 which is vertically screwed into the top of the ring via one of seven threaded grooves 106 in an inner circumference of the ring. The upper end of the inner sleeve 98 has six grooves 108 one of which is aligned with the desired groove 106 of the ring 76. The set screw 102 is positioned between the two aligned grooves 108 and 106 to hold the ring in place. The seven groove 106, six groove 108 combination allows for vernier adjustments in 8.572 degree increments to ensure that the ring is properly positioned with respect to the bearings 100.

A secondary retainer is formed by a plurality of screws 104 which mate with the plurality of the grooves 108 in the inner sleeve 98. The ring 76 thus serves the purposes of bearing adjustment, holding the inner sleeve 98 within the outer sleeve 90, and interacting with the teeth 82 of the locking member 72 to prevent the rear wheel 30 from swiveling when the locking member is moved downward by the cam. When the locking member 72 is in contact with the ring 76, the inner sleeve 98 is not able to rotate about the cylinder 68. Because the cylinder 68 cannot rotate—as it is affixed to the housing 60 which is held in place by the cam shaft 44—the wheel 30 cannot swivel.

The cylinder 68 extends downward through the locking member 72 and the ring 76 and through the hollow 112 in the inner sleeve 98. Thus, when not in a lock mode, the inner sleeve 98 rotates within the outer sleeve 90 and around the cylinder 68.

The structures which are preferably located within the cylinder 68 and the housing 60 and beneath the cam 40 will now be identified. Those skilled in the art will recognize that several of the described structures could be combined or divided while achieving the same functions. Rotation of the cam 40 moves the structures into different positions to thereby engage or disengage the locking mechanism and the swivel mechanism.

Positioned immediately below the cam 40 is a follower pin 120 (the pin 120 is shown above the cam 40 in the exploded version of FIG. 3). The follower pin 120 has a curved upper surface adapted for contact with the underside of the cam 40. Positioned below the follower pin 120 is a first holding pin 124. A small shim or washer 128 may be placed between the first holding pin 124 and the follower pin 120 to achieve proper engagement of the teeth 82 of the locking member and the teeth 86 of the ring 76.

A small channel 132 passes horizontally through the holding pin 124 for reception of a key 77 which can thereby be placed partially within the holding pin. As described earlier, the key 77 passes through the channel 80 in the cylinder 68 and into the locking member 72. The downward movement of the first holding pin 124 within the cylinder 68 causes the key 77 to move downward. If the downward movement is far enough, the key 77 causes the locking member 72 to contact the ring 76 and thereby prevent the inner sleeve 98 from rotating and the rear wheel 30 from swiveling.

Positioned below the key 77 and first holding pin 124 is a piston 140. The piston 140 extends most of the length of the cylinder 68 and is partially surrounded by a spring 144 which urges the piston upwardly, pushing it up when the cam 40 is rotated such that the cam does not push down the follower pin 120, holding pin 124 and the piston downward. A small washer 148 may be placed between the head of the piston 140 and the spring 144 to ensure a secure fit.

The bottom of the piston 140 is affixed to a second cylindrical holding pin 152 (located near the bottom of FIG.

3). The second holding pin 152 has a pair of opposing ridges 154 along its sides which are designed to slide within a corresponding pair of channels 158 at the bottom of the cylinder 68. Movement of the piston 140 moves the holding pin 152 up or down, causing the ridges 154 to slide vertically within the channels 158.

The holding pin 152 also has a pair of horizontally disposed arms 156a and 156b. The arm 156a is longer than the other arm 156b in order to prevent the inner sleeve 98 from rotating about the cylinder 68, as will be discussed below.

A braking mechanism 162 is positioned below the holder pin 152 and near the top of the rear wheel 30 inside the yoke 94 (though shown outside the yoke in the exploded version). The braking mechanism 162 includes a brake pad 164 and a brake arm 168 which is connected to the brake pad at one end, and the yoke 94 at the other. The braking mechanism 162 also includes a small bolt 170, a nut 172, and a small hole 176 in the brake pad 164. Rotation of the bolt 170 adjusts the position of the brake pad 164 relative to the wheel 30. An opening 178 is also provided in the yoke 94 to facilitate adjustment of the brake pad 164 by rotation of the bolt 170. As will be explained in more detail below, when the cam 40 is rotated to push the piston 140 downward, the second holding pin 152 contacts the brake pad 164 and forces the brake pad against the wheel 30 to thereby prevent the wheel 30 from rotating. When the brake pad 164 is not being applied, the wheel rotates freely about the axle 101, which can be a single cylindrical piece or a combination of pieces such as the two connectors 101a and bearing 101b shown in FIG. 3.

Figure 3A:
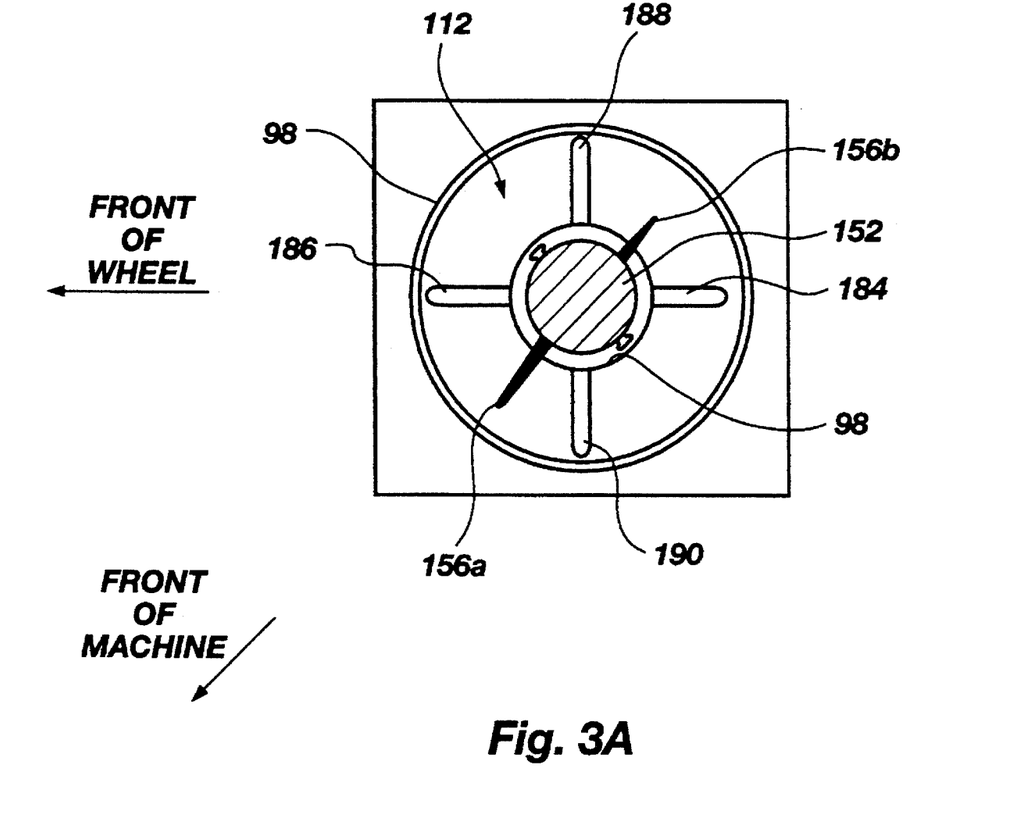
FIG. 3A is a bottom view of the inner sleeve and holding pin of FIG. 2.

Referring now to FIG. 3A, there is shown a bottom elevational view of the inner sleeve 98, a top portion of the yoke 94, and the second holding pin 152 with the arms 156a and 156b extending outward. The arms 156a and 156b of the second holding pin 152 are fixed relative to the machine 2 (FIG. 1) such that the longer arm 156a always points forward and the shorter arm 156b always points rearward.

Disposed in the bottom end of the inner sleeve 98 and the flange 100 are four grooves 184, 186, 188 and 190 which are sufficiently deep so that the arms 156a and 156b of the holding pin 152 can nest in the grooves to thereby prevent the inner sleeve 98 from rotating about the cylinder 68 because of the placement of the ridges 154 in the channels 158. The rear wheel 30 is thus prevented from swiveling.

A first pair of grooves 184 and 186 are positioned perpendicular to the axle 101, on opposite sides of the hollow 112, and are co-planar. As can be seen from FIGS. 1 through 3, the inner sleeve 98 and adjacent structure are disposed on one side of the wheel 30, which for convenience we designate as the front of the wheel. The shorter groove 184 extends horizontally and rearwardly of the sleeve 98 while the longer groove 186 extends forwardly of the sleeve.

The short groove 184 is long enough to nest with the shorter arm 156b of the holding pin 152, but it is shorter than the longer arm 156a. The longer groove 186 is long enough to nest with the longer arm 156a. When the shorter arm 156b is nested into the shorter groove 184 and the longer arm 156b is nested into the longer groove 186 by means described below, the rear wheel 30 is locked against swiveling such that the machine 2 may only be turned by the swiveling front wheel 26. The combination of different groove and arm lengths prevents the wheel 30 from locking into a position in which most of the wheel is forward of the inner sleeve 98, which would be unstable in forward movement of the machine 2.

The two other grooves 188 and 190 in the bottom end of the inner sleeve 98 are disposed perpendicular to the grooves 184 and 186, on opposite sides of the inner sleeve 98, and are co-planar. Each of the grooves 188 and 190 are of a length approximately the same as the longer groove 186. Thus, either arm 156a or 156b can nest in either groove 188 or 190. When the arms 156a and 156b are nested in the grooves 188 and 190, the wheel 30 will move the machine 2 sideways, i.e., they will only roll along a path perpendicular to the length of the machine 2. This position allows the machine 2 to be moved, e.g., along the length of a patient's body during a surgical or other procedure.

This interaction between the arms 156a and 156b of the second holding pin 152 and the grooves 184, 186, 188 and 190 provides the machine 2 which superb control. The parts described provide an undercarriage 8 which is easy to maneuver and yet can be precisely controlled.

Figure 4A:
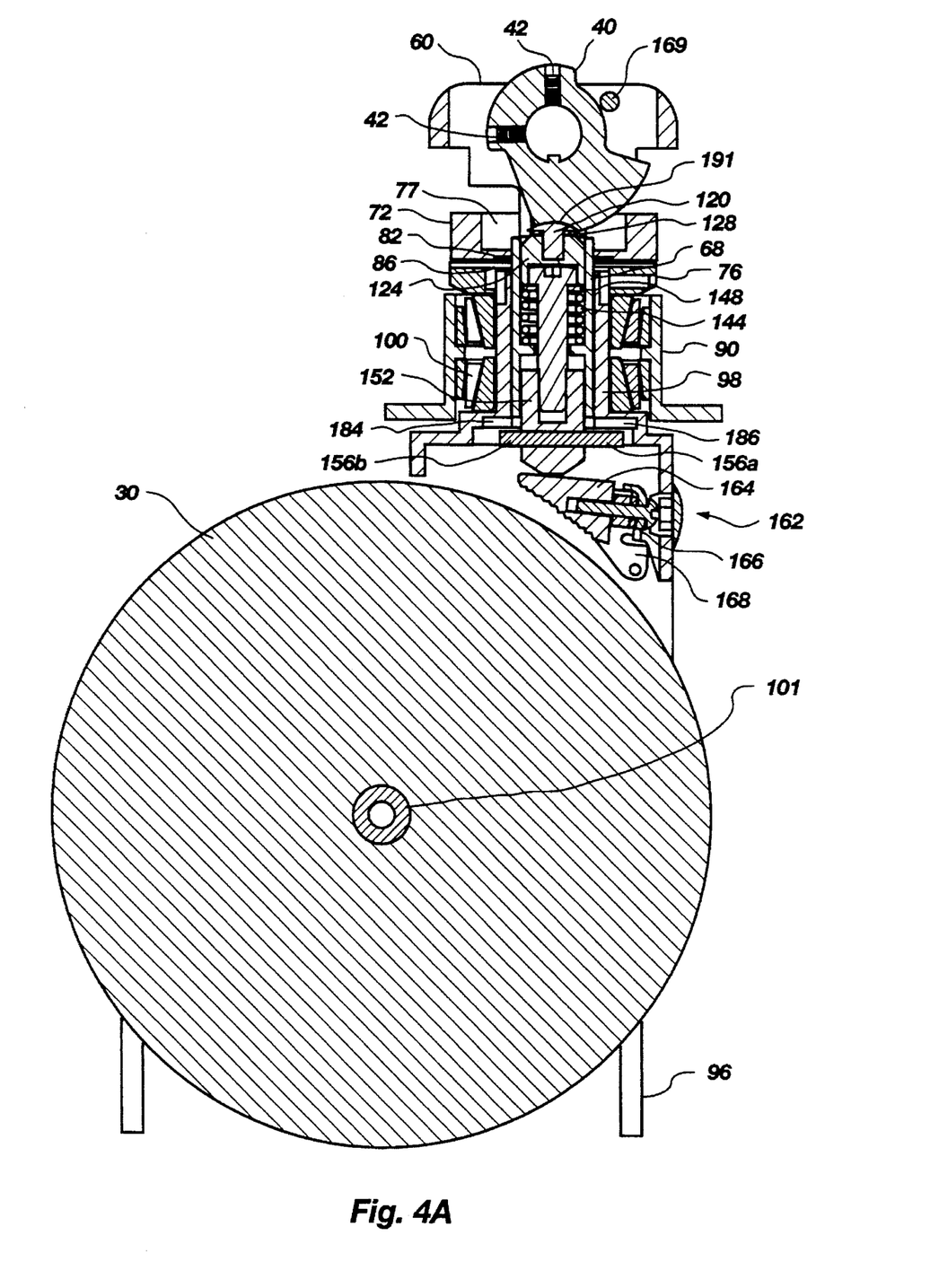
FIG. 4A is a side cross-sectional view of the wheel, brake, swivel and lock assemblies of FIG. 2, in which the wheel is allowed to roll and swivel.

Referring now to FIG. 4A, there is shown a side cross-sectional view of the rear wheel 30, swivel, locking and braking mechanisms of the present invention in which the rear wheel is a free mode in which it can both swivel and roll. In order to maintain the swivel lock and the braking mechanism 162 in disengaged positions, the structures within the cylinder 68 must be pressed slightly downward. Thus, the cam 40 is rotated into a first position in which a groove 191 on the underside of the cam is positioned over the follower pin 120, forcing the follower pin downward. The downward movement of the follower pin 120 causes a corresponding downward movement in the shim 128, the first holding pin 124, the key 77 and the piston 140, such that the head of the piston presses down on the washer 148 thereby partially compressing the spring 144. The downward movement of the key 136 causes a downward movement in the locking member 72, but not enough that the teeth 82 of the locking member interact with the teeth 86 of the ring 76.

The downward movement of the piston 140 also causes a downward movement in the second holding pin 152. The holding pin 152 is moved downward sufficiently that the arms 156a and 156b cannot nest within the grooves 186 and 184 or 188 and 190. The brake pad 164, however, does not contact the rear wheel 30 because the downward movement of the second holding pin 152 is not enough to overcome the force provided by a spring 166. The spring 166 is biased so as to prevent the brake pad 164 from contacting the wheel 30 until the second holding pin 152 overcome the spring's bias and forces the brake pad into contact with the wheel.

Figure 4B:
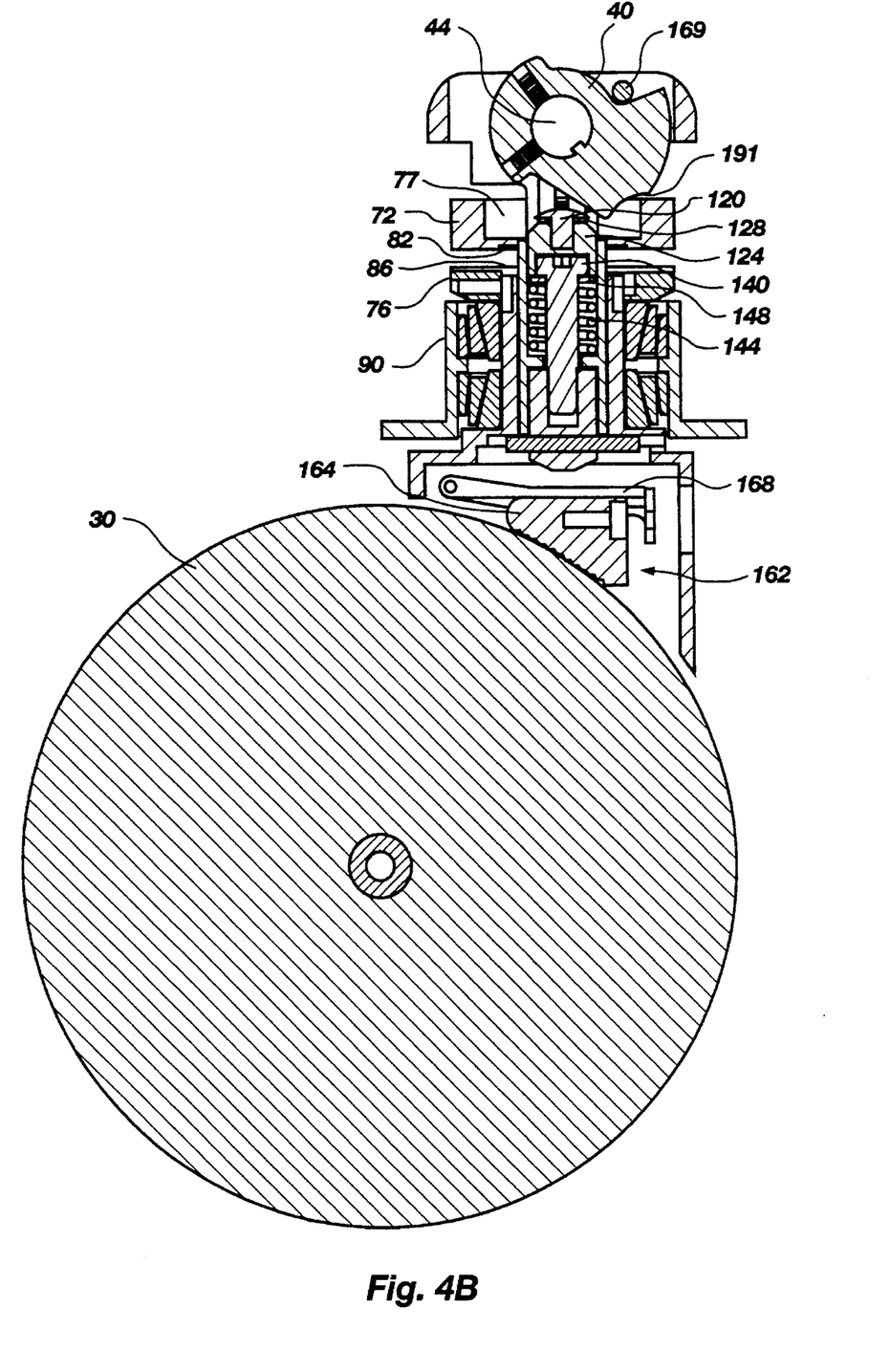
FIG. 4B is a side cross-sectional view of the wheel, brake and lock assemblies of FIG. 2 in which the wheel is allowed to roll forward and backward, but not swivel.

While the spring loaded arrangement described above is preferred, the brake pad 164 may be adapted to rest against the wheel 30 (as shown in FIG. 4B). The resting brake pad 164 is insufficient to prevent the wheel 30 from rolling except when force is applied by the second holding pin 152.

Also shown in FIG. 4A is a stop 169 positioned in the housing 60. The stop 169 limits rotation of the cam 40 to the three positions described in FIGS. 4A–C.

Referring now to FIG. 4B, a side cross-sectional view is shown of the rear wheel 30, braking mechanism 162 and swivel lock of the instant invention in which the brake is in a disengaged position and the swivel lock is in an engaged position, allowing the wheel to roll forward and backward, but not swivel. Rotation of the cam shaft 44 counterclockwise moves the cam 40 from the first position shown in FIG. 4A to a second position in which the cam is no longer in contact with the follower pin 120. Due to the lack of a downward force, the spring 144 pushes the washer 148 and piston 140 upward, lifting the first holder pin 124 and the key 77 so that the locking member 72 is moved further away from the ring 76. The piston's movement also moves the second holder pin 152 upward so that the arms 156a and 156b nest in the grooves 186 and 184 respectively. Once the arms 156a and 156b nest in the grooves 184 and 186 or the grooves 188 and 190, the inner sleeve 98 cannot rotate about the cylindrical portion 68 of the housing 60 and the wheel 30 is locked against swiveling.

Also shown in FIG. 4B is the braking mechanism 162 with the brake pad 164 resting against the rear wheel 30. As was explained above, the brake pad 164 will not prevent the rear wheel 30 from rolling unless the brake pad 164 is pressed against the wheel 30 by the second holding pin 152.

Figure 4C:
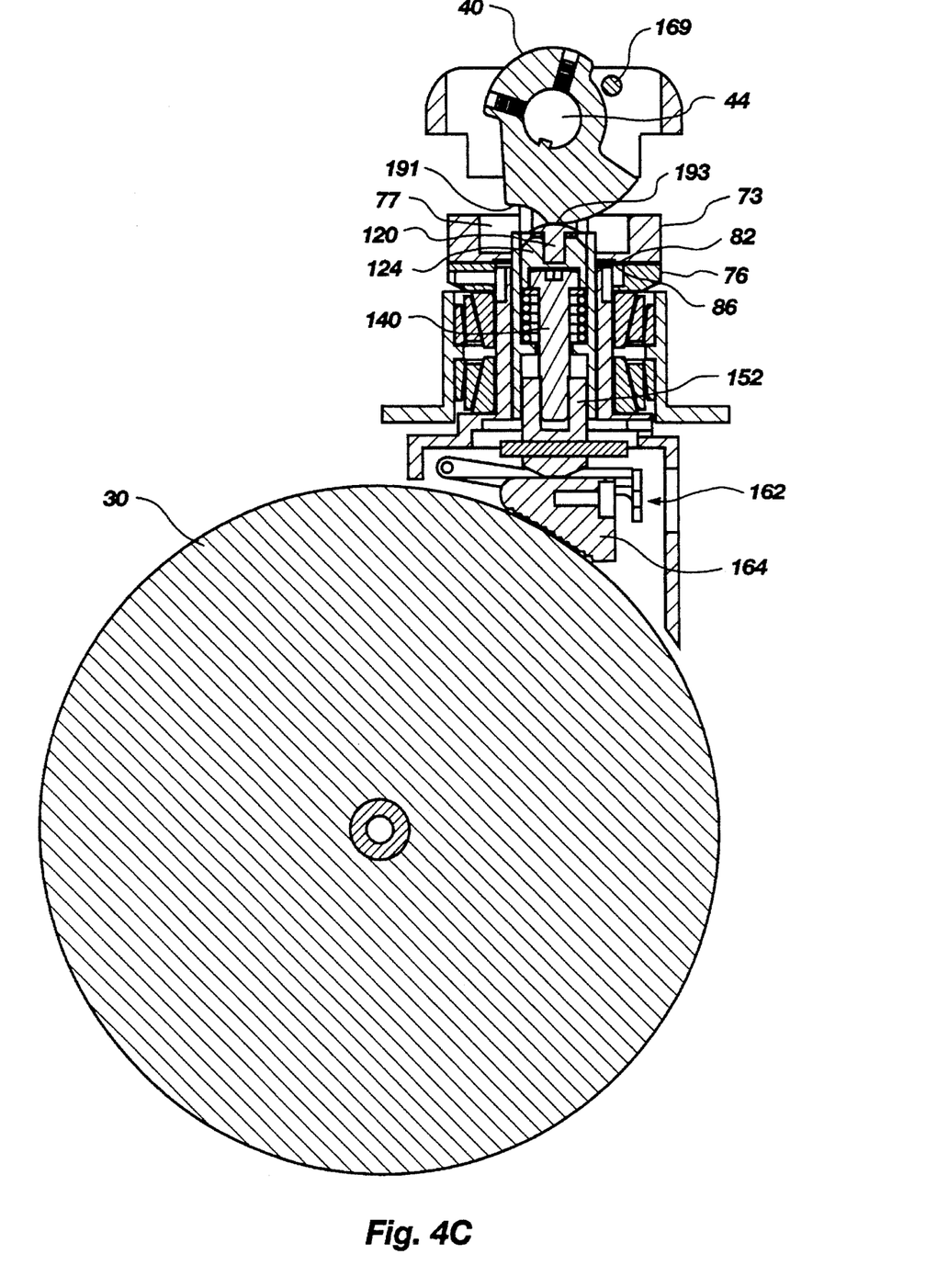
FIG. 4C is a side cross-sectional view of the wheel, brake, swivel and lock assemblies of FIG. 2 in which the wheel can neither roll or swivel.

Referring now to FIG. 4C, there is shown a side cross-sectional view of the rear wheel 30, the braking mechanism 162, and the swivel lock of the present invention in a total lock mode in which the braking mechanism and swivel lock are both in the engaged position, preventing the wheel from rolling or swiveling.

The cam shaft 44 has been rotated clockwise so that the cam 40 has been rotated to a position beyond the groove 191 and at which a projection 193 from the cam pushes the follower pin 120 to a position below that shown in FIG. 4A. The first holding pin 124 and the key 77 are pushed sufficiently far that the teeth 82 of the locking member 72 come into contact with the teeth 86 of the ring 76. With the teeth 82 and 86 engaged, the inner sleeve 98 cannot rotate about the cylindrical portion 68 of the housing 60, thereby preventing the rear wheel 30 from swiveling.

The lower position of the first holding pin 124 holds the piston 140 in a lower position, thereby forcing the second holding pin 152 against the brake pad 164. The brake pad 164, in turn, prevents the wheel 30 from rolling.

Thus, when the cam 40 is in the position shown in FIG. 4C, the rear wheel 30 can neither swivel nor roll, preventing the machine 2 from being accidentally moved. Once the need for keeping the machine 2 in a fixed place is finished, the user need merely step on the pedal (FIG. 1) to rotate the cam shaft 44 and thereby rotate the cam 40 from the position shown in FIG. 4C to the position shown in FIG. 4A or 4B.

Figure 5:
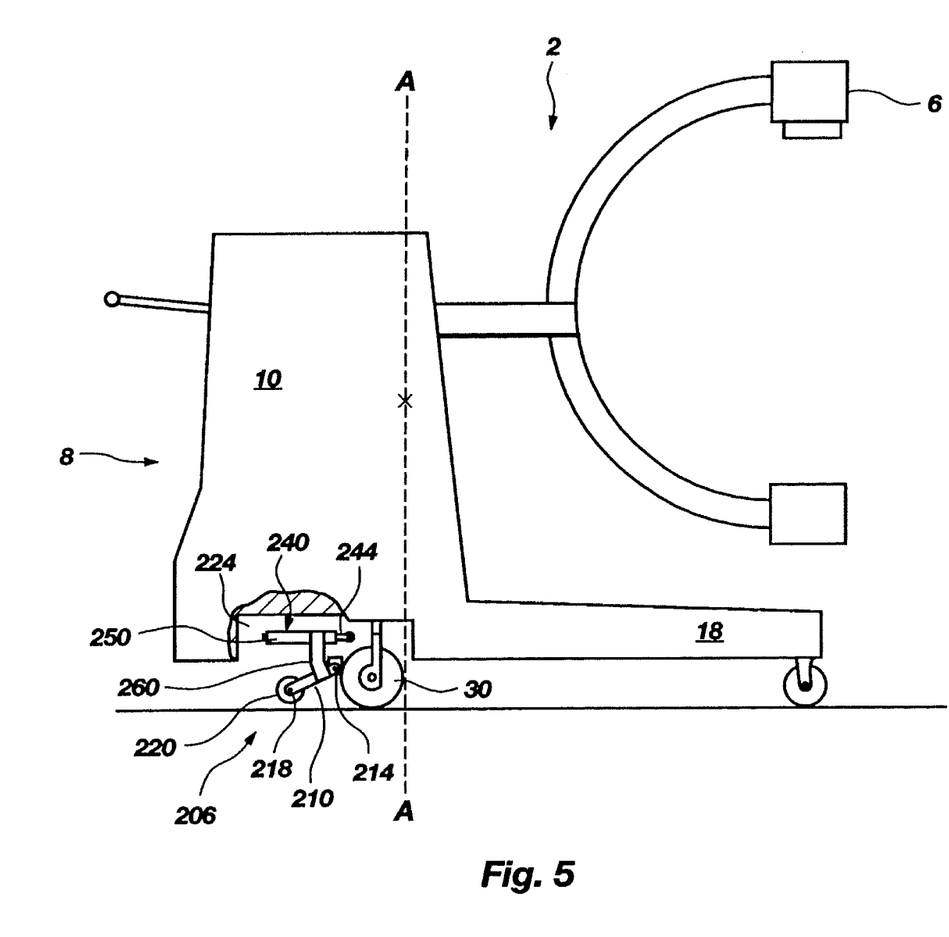
FIG. 5 is a side perspective view of an X-ray diagnostic machine positioned on a level surface, having a cut-away view of the undercarriage to reveal a balance wheel assembly in accordance with the instant invention.
Figure 5A:
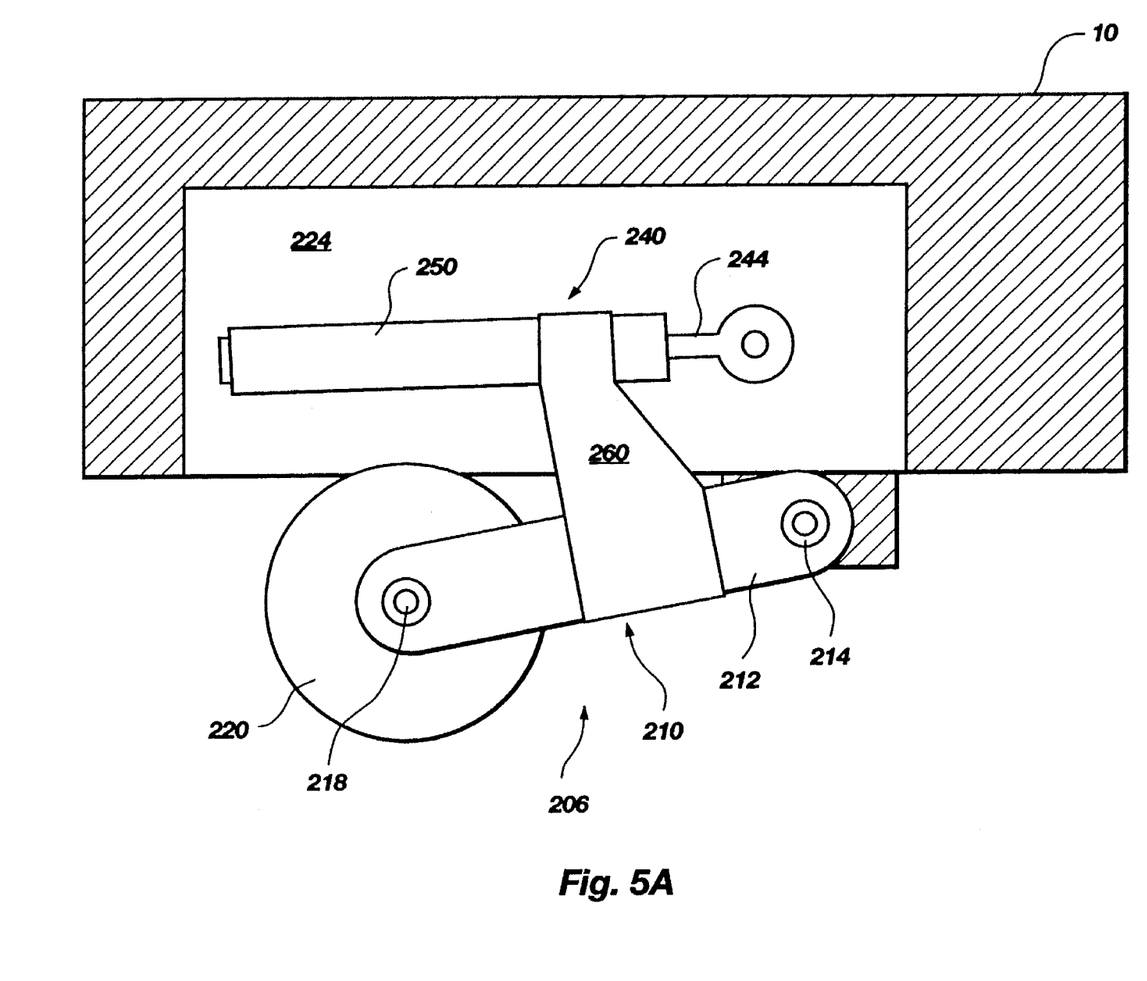
FIG. 5A is an enlarged partially cut-away view of the balance wheel assembly of the instant invention.

Referring now to FIGS. 5 and 5A, there is shown an undercarriage 8 with a balance wheel assembly 206 in accordance with the present invention.

As previously mentioned, the rear wheels 30 are located close to the vertical plane A—A bisecting the center of gravity of the machine 2 so that the support arm 18 can be lifted by those moving the equipment. This positioning, however, decreases the stability of the equipment while being moved. In order to prevent the undercarriage 8 from becoming unstable and pitching backward when the forward, support section 18 passes over bumps or up inclines, a balance wheel assembly 206 is disposed rearward of the wheels 30. The assembly 206 comprises an elongate leg 210 which is pivotally attached at a proximal end 214 to the undercarriage 8 such that the leg member 210 can pivot from a position in which it extends downwardly from the undercarriage 8 to a position in which it is horizontal or extends slightly upwardly from the point of attachment.

The leg member 210 extends downwardly and rearwardly from the undercarriage 8 and is attached at a distal end 218 to a wheel 220, adapted for forward and rearward rolling movement. Force exerted upwardly against the wheel member 220 causes the leg member 210 to pivot upwardly, moving the wheel 220 partially into a channel 224 which is disposed above the wheel member in undercarriage 8.

A damping device such as a linear decelerator 240 is positioned above the leg member 210 in the channel 224. In a preferred embodiment, the linear decelerator 240 has a piston 244 and a housing 250. The forward end of the piston 244 is pivotally attached to the undercarriage 8, while the rearward end is slidably disposed within the housing 250. Preferably, the piston 244 and housing 250 are disposed generally horizontally within the channel 224 when no force is being applied to the wheel member 220 and thus the leg member 210.

The housing 250 is attached to the leg member 210 by an arm 260. When force is applied to the wheel member 220, the force is conveyed through the leg member 210 and the arm 260, moving the housing 250 relative to the piston 244. In a preferred embodiment, the linear decelerator 240 has a plurality of apertures/ports 252 in the housing (250) which limit the movement of the housing 250 relative to the piston 244 to a relatively controlled rate. Thus, the wheel member 220 moves into the channel 224 at a slow, controlled rate. Once the force on the wheel member 220 is no longer present, the linear decelerator 240 returns the wheel member and the leg member 210 to their original downward positions.

Examples of linear decelerators suitable for use with the invention are available from, e.g., ACE controls Inc., Farmington, Mich. The internal structure of linear decelerators is described in catalogues such as that produced by ACE Controls, and in Patents such as U.S. Pat. No. 3,027,152, issued to Deschner.

As shown in FIG. 5, the balance wheel assembly 206 can preferably be adjusted so that the wheel member 220 does not contact the ground when the equipment is being moved on a level surface, minimizing any unnecessary noise and resistance.

Figure 6:
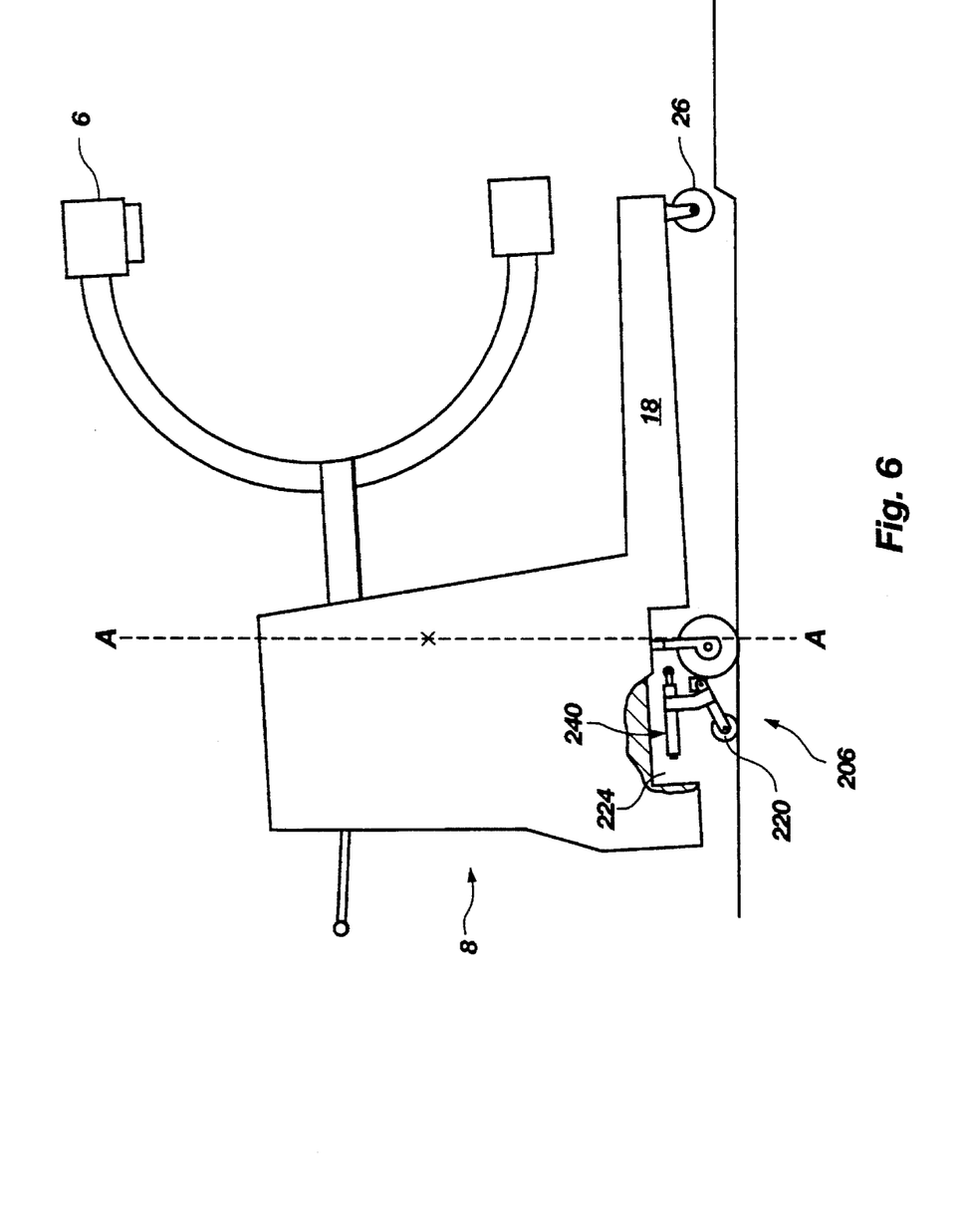
FIG. 6 is a side elevational view of the machine of FIG. 5 with the front wheels passing over a bump.

Referring now to FIG. 6, when the front wheel 26 encounters a bump or similar obstacle a slight lifting of the support arm 18 causes the wheel arm 220 to contact the ground. The positioning of the wheel arm 220 prevents the undercarriage 8 from quickly pivoting back and damaging the equipment as well as hurting the feet or legs of those moving the equipment. The linear decelerator 240 allows the front wheel 26 to be lifted slowly so that is can pass over small obstacles. As the support arm 18 rises, the wheel 220 slowly moves into the channel 224 so that the center of gravity of the machine may gradually shift.

Figure 7:
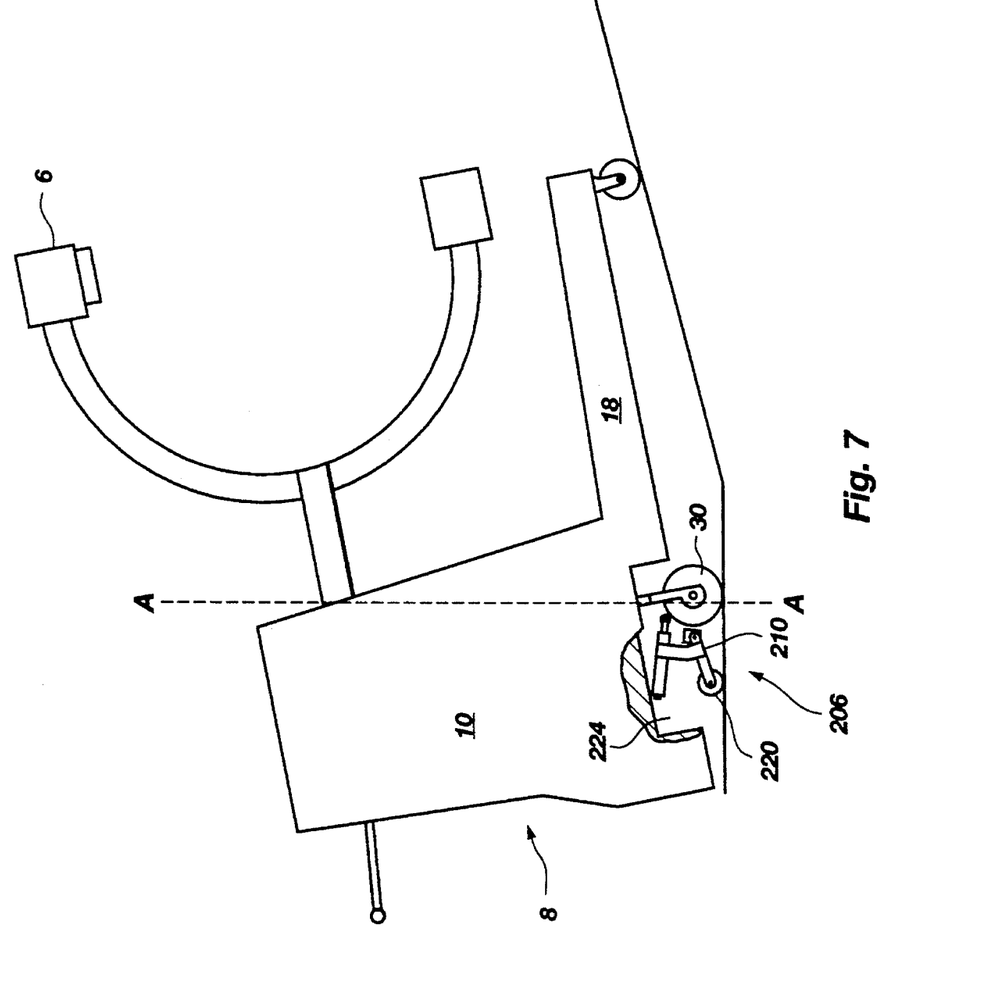
FIG. 7 is a side elevational view of the machine of FIG. 5 with the front wheels positioned on an incline surface and the rear wheels positioned on a level surface.

Referring now to FIG. 7, when the equipment is rolled up an incline the leg 210 pivots and the wheel 220 gradually retracts into the channel 224. By the time the rear wheels 30 would have become high centered with conventional stops, the wheel 220 has receded into the channel 224 enough that the undercarriage 8 can continue to move up the incline. Once the rear wheels 30 are rolling on the inclined surface, the wheel 220 and the leg 210 return to their original positions. Thus, the balance wheel assembly 206 helps prevent accidental injury to the feet or legs of those moving the equipment without interfering with the movement of the equipment over bumps or up inclines.

Depending on the desired use, modifications can be made to the balance wheel assembly 206 while remaining within the scope of the invention. For example, a linear decelerator 240 with a threaded housing can be provided in conjunction with an arm 260 with mating threads. Rotation of the housing 250 causes the arm 260 to move slightly, changing the location of the leg member 210 and wheel member 220. Thus, if noise is a consideration, the housing 250 can be rotated such that the wheel member 220 is held slightly off the ground. Additionally, the size of the linear decelerator 240 can be varied depending on the weight of the machine, and the maximum velocity at which the leg member 210 is to pivot towards the undercarriage 8.

In the described embodiment, the balance wheel assembly 206 is laterally centered under the base 10. This position ensures that the wheel 220 will prevent rocking even if the support arm 18 encounters an obstacle at an angle. The balance wheel assembly 206, however, can be placed off-center if needed. Additionally, more than one assembly 206 can be used if the undercarriage 8 tends to be laterally unstable. This is often the case when the undercarriage 8 uses only one centered rear wheel 30. In such a situation, the balance wheel assemblies 206 can be used to prevent a lateral shift in the center of gravity as well as a rearward shift.

In the manner described above, a simple, effective undercarriage 8 with swivel and braking devices and a balance wheel assembly 206 is provided. The undercarriage 8 allows for better control of heavy diagnostic equipment. It is to be understood that the above-described arrangements are only illustrative of the application of the principles of the present invention. Modifications and alternative arrangements may be devised by those skilled in the art in light of this disclosure without departing from the scope of the present invention as defined by the appended claims.

What is claimed is:

1. An undercarriage assembly for wheeling heavy equipment, said undercarriage being attached to a base member supporting said equipment, comprising:

a front wheel rotatably mounted on a bottom portion of the base member and being rotatable about a horizontal axis;

swivel means for rotation of a wheel about a vertical axis, the swivel means being connected to the base member rearward of said front wheel and extending generally downward, said swivel means having an engaged position, wherein the swivel means can rotate about the vertical axis, and a disengaged position wherein the swivel means cannot swivel about the vertical axis;

a rear wheel rotatably attached to said swivel means on the bottom of the base member and behind the front wheel, the rear wheel being rotatable about a horizontal axis in tandem with the front wheel to thereby enable wheeling the equipment across a surface such that respective bottom extremities of said wheels are common to a plane tangential thereto;

means for braking disposed adjacent said rear wheel, said braking means having an engaged position, in which the rear wheel cannot rotate and a disengaged position in which the rear wheel can rotate;

an elongate leg member pivotally attached at a proximal end to the base member, rearward of said rear wheel;

a wheel member rotatably attached on a distal end of the leg member and being rotatable about a horizontal axis; and positioning means attached to the base member and to the leg member for positioning said leg member to extend downwardly from the base member at an angle thereto such that the wheel member is disposed above the tangential plane common to the front and rear wheels in a suspended position and rotates in tandem with the rear wheel when said wheel member contacts the surface across which the equipment is wheeled, said positioning means comprising a linear decelerator which absorbs impact energy from the wheel member when said wheel member contacts said surface such that the wheel member is moved toward the base at a constant rate to thereby prevent the equipment from rocking.

2. The undercarriage assembly of claim 1 wherein the swivel means comprises an outer sleeve, an inner sleeve disposed partially within said outer sleeve, the inner sleeve being attached to the rear wheel, and at least one bearing disposed between the inner and outer sleeves to enable the inner sleeve to rotate within the outer sleeve and about the vertical axis.

3. The undercarriage assembly of claim 2 wherein the swivel means further comprises a housing partially disposed within said inner sleeve and extending upward out of said inner sleeve to a fixed attachment with the base member, the housing being positioned such that the inner sleeve rotates about said housing.

4. The undercarriage assembly of claim 3 wherein the inner sleeve has a top end and a bottom end, and wherein the swivel means further comprises:

a horizontal linear groove disposed along a bottom edge of the swivel means and perpendicular to the vertical axis, a holder pin having generally horizontal arms formed so as to nest in the horizontal groove, the holder pin being movable between a nested position and an extended position, such that when the arms of the holder pin are nested in said groove, the swivel means is in the disengaged position and when the arms of the holder pin are not nested in said groove, the swivel means is in the engaged position.

5. The undercarriage assembly of claim 4 further comprising an actuator means disposed adjacent to said housing, the actuator means comprising a cam disposed above the holder pin and in mechanical communication with the holder pin such that rotation of the cam moves the holder pin between nested and extended positions to thereby move the swivel means between disengaged and engaged positions.

6. The undercarriage assembly of claim 1 wherein the braking means comprises:

a brake shoe disposed adjacent to the rear wheel and adjacent to the swivel means;

a piston disposed above the brake shoe and movable between a first position, in which the brake shoe is forcefully pressed against the wheel, and a second position in which the brake shoe is not forcefully pressed against the wheel; and an arm for holding the brake shoe beneath the piston and adjacent to the wheel, the arm being disposed beneath the swiveling means.

7. The undercarriage assembly of claim 6 wherein the piston is disposed beneath a rotatable cam such that rotation of the cam causes the piston to move between the first and second positions to thereby engage and disengage the braking means.

8. The undercarriage assembly of claim 1 wherein the rear wheel is disposed adjacent to a vertical plane passing through a center of gravity of the equipment and wherein the wheel member is disposed rearwardly of said plane.

9. The undercarriage assembly of claim 1 wherein the linear decelerator includes, a cylindrical housing attached to the equipment, the housing having a first end and a second end;

a piston having a first end and a second end, the first end being attached to the equipment and the second end being linearly, slidably disposed into said housing, a plurality of variable ports disposed within the cylindrical housing to thereby limit sliding of the piston within the housing to a relatively fixed rate, and a connecting arm attached at the first end to the housing and at an opposing second end to the leg member.

10. The undercarriage assembly of claim 9 wherein the variable ports are adapted to provide greater damping resistance the greater the change of force on the wheel member.

11. A brake and wheel undercarriage attached to a base member supporting diagnostic equipment, the undercarriage comprising:

swivel means for rotation of a wheel about a vertical axis, the swivel means being connected to the frame member and extending generally downwardly from the frame member, the swivel means comprising:

an inner sleeve, an outer sleeve, and at least one bearing disposed between the inner and outer sleeves such that the inner sleeve rotates about the vertical axis and at least partially within the outer sleeve, a housing partially disposed within said inner sleeve and extending upward out of said inner sleeve to a fixed attachment with the base member, the housing being positioned such that the inner sleeve rotates about said housing; and a horizontal linear groove disposed along a bottom edge of the swivel means and perpendicular to the vertical axis;

a wheel connected to the swivel means opposite the frame member, the wheel being disposed about a generally horizontal axis and rotatable about said axis so as to roll as the frame member is moved in a generally horizontal direction;

at least one locking means for disabling the swivel means, the locking means being disposed along the swivel means and having a unlocked position, in which the swivel means can rotate about the vertical axis and a locked position in which the swivel means cannot rotate about the vertical axis, the at least one locking means comprising a holder pin disposed along the swivel means and having generally horizontal arms formed so as to nest in the horizontal groove, the holder pin being movable between a nested position and an extended position, such that when the arms of the holder pin are nested in said groove, the swivel means is in the disengaged position and when the arms of the holder pin are not nested in said groove, the swivel means is in the engaged position;

first actuating means for moving the locking means between the unlocked and locked position, said actuating means being disposed adjacent to the locking means, means for braking disposed adjacent to the wheel and having an engaged position, in which the wheel cannot rotate, and a disengaged position in which the wheel can rotate; and second actuating means disposed adjacent the braking means for moving the braking means between the disengaged position and the engaged position.

12. The undercarriage of claim 11 wherein the first actuating means comprises a cam disposed above the holder pin and in mechanical communication with the holder pin such that rotation of the cam moves the holder pin between nested and extended positions.

13. The undercarriage of claim 12 wherein the first actuator means further comprises a movable piston disposed below the cam, extending through the swiveling means and attached to the holder pin, the holder pin being moved from a nested position to an extended position by rotating the cam so as to move the piston and holder pin in a downward direction.

14. The undercarriage of claim 11 wherein the locking means comprises;

a flange extending radially from the swivel means, a generally planar locking member disposed adjacent the first actuating means and above the flange and having at least one projection, such that when the locking member is forced downwardly into contact with the flange, the projection contacts the flange and prevents rotation of the flange and swivel means about the vertical axis.

15. The undercarriage of claim 14 wherein the actuator means comprises a cam disposed above the generally planar locking member such that rotation of the cam moves the locking member into forceful contact with the flange.

16. The undercarriage of claim 14 wherein the at least one projection from the locking member comprises a plurality of teeth and wherein the flange comprises a plurality of teeth disposed so as to interlock with the teeth of the generally planar locking member when the locking member is in forceful contact with the flange.

17. The undercarriage of claim 15 wherein the flange comprises resilient material disposed such that forceful contact between the resilient material and the teeth of the locking means prevents the flange from rotating about the vertical axis.

18. The undercarriage of claim 11 wherein the braking means comprises:

a brake shoe disposed adjacent to the wheel and adjacent to the swivel means;

a piston disposed above the brake shoe and movable between a first position, in which the brake shoe is forcefully pressed against the wheel, and a second position in which the brake shoe is not forcefully pressed against the wheel.

19. The undercarriage of claim 18 wherein the braking means further comprises an arm for holding the brake shoe beneath the piston and adjacent to the wheel, the arm being disposed beneath the swiveling means.

20. The undercarriage of claim 11 wherein the second actuator means comprises a piston disposed above the brake shoe and a cam disposed above the piston, the cam and the piston being positioned such that rotation of the cam pushes the piston downwardly, forcing the braking means against the wheel.

21. The undercarriage of claim 11 wherein the first actuator means and the second actuator means comprise a cam and a piston, the cam being disposed above the locking means and the braking means, the cam being rotatable and positioned above the piston such that rotation of the cam moves the piston into different positions to thereby lock and unlock the locking means and engage and disengage the braking means.

22. An undercarriage assembly for wheeling heavy equipment, said undercarriage assembly comprising:

at least one front wheel rotatably mounted on a bottom portion of the equipment and being rotatable about a horizontal axis, at least one rear wheel rotatably mounted on the bottom portion of the equipment behind the front wheel and being rotatable about a horizontal axis in tandem with the front wheel to thereby enable wheeling the equipment across a surface such that respective bottom extremities of said wheels are common to a plane tangential thereto;

a leg member pivotally attached at a proximal end to the bottom portion of the equipment, behind the rear wheel;

a wheel member rotatably mounted on a distal end of the leg member and being rotatable about a horizontal axis, means attached to the equipment and to the leg member for positioning said leg member to extend downwardly from the bottom portion of the equipment at an angle thereto such that the wheel member resides above the tangential plane common to the front and rear wheels in a suspended position and rotates in tandem with the rear wheel when said wheel member contacts the surface across which the equipment is wheeled to thereby assist in wheeling said equipment, such that said means absorbs impact energy from the wheel member when said wheel member contacts said surface to thereby prevent the equipment from rocking, said means comprising a means for providing constant rate resistance so as to allow constant rate deflection of the wheel member toward the base member.

23. The wheel carriage assembly of claim 22 wherein the rear wheel is disposed adjacent to a vertical plane passing through a center of gravity of the equipment and wherein the wheel member is disposed rearwardly of said plane.

24. The wheel carriage assembly of claim 22 wherein the means for positioning and absorbing impact energy comprises a linear decelerator including, a cylindrical housing attached to the equipment at a first end;

a piston having a first end and a second end, the first end being attached to the equipment and the second end being linearly, slidably disposed into a second end of said housing, a plurality of variable ports disposed within the cylindrical housing to thereby limit sliding of the piston within the housing to a relatively fixed rate, and a connecting arm attached at a first end to the cylinder housing and at an opposing second end to the leg member.

25. The wheel carriage assembly of claim 24 wherein the variable ports are adapted to provide greater damping resistance the greater the change of force on the wheel member.

26. The balance wheel assembly of claim 24 wherein the arm is disposed to connect to the leg member at a point between the pivotal attachment to the equipment and the connection to the wheel member.

27. The wheel carriage assembly of claim 23 further including means for steering at least one of said wheels to enable the equipment to move in a nonlinear, horizontal direction.

28. An undercarriage carriage assembly for C-arm X-ray diagnostic equipment having a base with two lateral sides and a front portion and a rear portion, the front and rear portion being defined by a center of gravity of the equipment, said assembly comprising:

at least one front wheel rotatably mounted on a bottom portion of the base member and being rotatable about a horizontal axis to allow the base to roll on said wheel;

a pair of rear wheels rotatably mounted to the base member rearward of the front wheel, the rear wheels being disposed on lateral sides of the base member and being positioned adjacent to the front portion and the rear portion so as to be generally below the center of gravity of said equipment, each of said wheels being rotatable about a horizontal axis in tandem with the front wheel to thereby enable wheeling the equipment across a surface such that respective bottom extremities of said wheels are common to a plane tangential thereto;

a leg member pivotally attached at a proximal end to the bottom portion of the equipment, behind the rear wheel;

a wheel member rotatably mounted on a distal end of the leg member and being rotatable about a horizontal axis; and a linear decelerator attached to the base member and to the leg member for positioning said leg member to extend downwardly from the bottom portion of the base member at an angle thereto such that the wheel member resides above the tangential plane common to the front and rear wheels in a suspended position and rotates in tandem with the rear wheel when said wheel member contacts the surface across which the equipment is wheeled to thereby assist in wheeling said equipment, such that said linear decelerator absorbs impact energy from the wheel member when said wheel member contacts said surface, so as to allow constant rate deflection of the wheel toward the base member to thereby prevent the equipment from rocking.

29. An undercarriage assembly for wheeling heavy equipment, said undercarriage being attached to a base member supporting said equipment, comprising:

a front wheel rotatably mounted on a bottom portion of the base member and being rotatable about a horizontal axis;

a rear wheel rotatably connected to the base member behind the front wheel, the rear wheel being rotatable about a horizontal axis in tandem with the front wheel to thereby enable wheeling the equipment across a surface such that respective bottom extremities of said wheels are common to a plane tangential thereto;

swivel means for connecting the rear wheel to the base member so as to enable rotation of the rear wheel about a vertical axis, said swivel means having an engaged position, wherein the swivel means can rotate about the vertical axis, and a disengaged position wherein the swivel means cannot swivel about the vertical axis, the swivel means comprising:

an outer sleeve, an inner sleeve disposed partially within said outer sleeve, the inner sleeve having an top end and a bottom end, and being attached to the rear wheel, at least one bearing disposed between the inner and outer sleeves to enable the inner sleeve to rotate within the outer sleeve and about the vertical axis;

a horizontal linear groove disposed along a bottom edge of the swivel means perpendicular to the vertical axis; and a holder pin disposed along the bottom of an actuator means having generally horizontal arms formed so as to nest in the horizontal groove, the holder pin being movable between a nested position and an extended position, such that when the arms of the holder pin are nested in said groove, the swivel means is in the disengaged position and when the arms of the holder pin are not nested in said groove, the swivel means is in the engaged position said actuator means for moving the holder pin between the disengaged and engaged positions being disposed adjacent said inner sleeve.

30. The undercarriage assembly of claim 29 further comprising an actuator means disposed adjacent to said holder pin, the actuator means comprising a cam disposed above the holder pin and in mechanical communication with the holder pin such that rotation of the cam moves the holder pin between nested and extended positions to thereby move the swivel means between disengaged and engaged positions.

* * * * *